United States Patent [19]
Ackmann et al.

[11] Patent Number: 5,178,154
[45] Date of Patent: Jan. 12, 1993

[54] IMPEDANCE CARDIOGRAPH AND METHOD OF OPERATION UTILIZING PEAK ALIGNED ENSEMBLE AVERAGING

[75] Inventors: James J. Ackmann; Norbert T. Christman, both of Wauwatosa; Thomas J. Ebert, Glendale, all of Wis.

[73] Assignee: Sorba Medical Systems, Inc., Milwaukee, Wis.

[21] Appl. No.: 584,319

[22] Filed: Sep. 18, 1990

[51] Int. Cl.$^5$ .......................................... A61B 5/0295
[52] U.S. Cl. .................................. 128/713; 128/695; 128/696; 128/734; 364/413.03
[58] Field of Search ............... 128/695, 696, 693, 670, 128/713, 734; 364/413.02, 413.03, 413.06

[56] References Cited

U.S. PATENT DOCUMENTS

| Re. 30,101 | 9/1979 | Kubicek et al. | 128/713 |
|---|---|---|---|
| 3,730,171 | 5/1973 | Namon. | |
| 3,835,839 | 9/1974 | Brown. | |
| 3,835,840 | 9/1974 | Mount. | |
| 3,871,359 | 3/1975 | Pacela. | |
| 3,882,851 | 5/1975 | Sigworth. | |
| 3,994,284 | 11/1976 | Voelker. | |
| 3,996,925 | 12/1976 | Djordjevich. | |
| 4,270,547 | 6/1981 | Steffen et al. | 128/671 |
| 4,303,075 | 12/1981 | Heilman et al. | 128/419 PG |
| 4,305,400 | 12/1981 | Logan | 128/670 |
| 4,450,527 | 5/1984 | Sramek | 364/415 |
| 4,548,211 | 10/1985 | Marks | 128/693 |
| 4,781,201 | 11/1988 | Wright et al. | 128/671 |
| 4,802,491 | 2/1989 | Cohen et al. | 364/413.06 |

OTHER PUBLICATIONS

Preliminary Instruction Manual for the Minnesota Impedance Cardiograph Model 303.
A brochure describing the Minnesota Impedance Cardiograph Model 304b.
A brochure describing the IFM/Minnesota Impedance Cardiograph.
A paper published at the 24th ACEMB on Oct. 31 through Nov. 4, 1971 entitled "Computer Determination of Cardiac Output Means of Impedance Plethysmography".
"Continuous Monitoring of Systolic Time Intervals, Surface Electrodes During Treadmill Exercise Test" published Mar. 1, 1978.
Abstract of a paper entitled "The Use of Signal Averaging of Electrical Impedance Signals to Determine Cardiac Timing Information During Uninterrupted Exercise".
Abstract of a paper entitled "Surface Electrode Monitoring of Myocardial Function Impassive Postural Changes".
"Impedance Cardiography to Study of Postural Stress", Journal of Applied Physiology, Jul. 1970.
"Continuous Electrode Monitoring of Systolic Time Intervals During Exercise", British Heart Journal, p. 1391, 1978.

(List continued on next page.)

Primary Examiner—Kyle L. Howell
Assistant Examiner—Kennedy J. Schaetzle
Attorney, Agent, or Firm—Quarles & Brady

[57] ABSTRACT

Parameters of cardiac activity can be derived from detecting thoracic impedance changes in a patient. An excitation signal is applied between a first pair electrodes located on the patient's forehead and torso. The voltage across another pair of electrodes positioned between the first pair is sensed to provide a first signal representing the impedance. The derivative of the first signal produces a second signal. Samples of the second signal taken during a number of cardiac cycles are ensemble averaged to minimized respiratory artifacts. Different criteria, such as the relationship between the second signal and an electrocardiographic signal, are employed to accept segments of the second signal which occur during different cardiac cycles. Samples of the accepted second signal segments for a number of cardiac cycles are ensemble averaged to minimize respiratory artifacts. The ensemble averaged data is employed to calculate cardiac stroke volume and cardiac output.

37 Claims, 6 Drawing Sheets

OTHER PUBLICATIONS

"Automatic Determination of Cardiac Output Using an Impedance Plethysmography", 1981.

"Continuous Determination of Cardiac Output During Exercise By Use of Impedance Plethysmography", 1981.

"Design of an Automatically Balancing Electrical Impedance Plethysmograph", *Journal of Clinical Engineering*, Apr./Jun. 1984.

"Impedance Cardiograms Reliably Estimate Beat-By-Beat Changes of Left Ventricular Stroke Volume in Humans".

"Determination of Cardiac Output Using Ensemble Average Impedance Cardiograms", 1984.

"Motion Artifact from Spot and Band Electrodes During Impedance Cardiography", 1986.

"Cardiac Output Monitoring by Impedance Cardiography During Treadmill Exercise", 1986.

"The Use of Thoracic Impedance for Determining Thoracic Blood Volume Changes in Man", 1986.

"Computer-Automatic Impedance-Derived Cardiac Indexes", 1986.

"Impedance Cardiography and Circulatory Response to Stress", Oct. 1988.

"The Trend Toward Noninvasive Monitoring", *Medical Electronic Products*, Sep. 1988.

"Impedance Cardiography: Noninvasive Assessment of Human Central Hemodynamics At Rest And During Exercise", *Exercise and Sport Sciences Reviews*, May 1989.

IMPEDANCE CARDIOGRAPH AND METHOD OF OPERATION UTILIZING PEAK ALIGNED ENSEMBLE AVERAGING

BACKGROUND OF THE INVENTION

The present invention relates to the determination of heart function utilizing an impedance cardiograph, and particularly to such apparatus which determines the cardiac output by ensemble averaging thoracic impedance data measured during a number of cardiac cycles.

Impedance cardiography is a non-invasive technique for determining cardiac parameters in humans. Traditionally it has consisted of placing of two electrode bands circumferentially around the neck and two additional electrode bands around the thorax. A high frequency, low magnitude electric current was applied to the two outer electrode bands. The voltage changes between the inner two electrode bands were measured and correlated to the impedance of the patient. Changes in the baseline thoracic impedance ($Z_0$) have been related to the changes of intravascular and extravascular fluids within the thorax. Thoracic impedance changes correlate closely with alterations of central blood volume. From the change of the value of a first derivative of the impedance, information concerning cardiac activity, such as cardiac output, can be obtained.

To obtain the cardiac output, the stroke volume representing the amount of blood being ejected during each cardiac cycle first must be computed. Stroke volume can be determined from the following equation disclosed by William G. Kubicek et al. in U.S. Pat. No. 3,340,867:

$$SV = \rho \frac{L^2 T}{Z_0^2} (dZ/dt_{max})$$

where SV is the ventricular stroke volume, $\rho$ is the resistivity of blood at the excitation frequency, L is the shortest distance between the inner electrodes, $Z_0$ is the average baseline impedance between the inner electrodes, T is the ventricular ejection time, and $dZ/dt_{max}$ is the magnitude of the first derivative of the thoracic impedance. The cardiac output then is computed by multiplying the stroke volume by the heart rate.

One of the problems encountered in using thoracic impedance to derive the stroke volume is that the thoracic impedance is also influenced by the effects of respiration. Similarly, if the patient is moving, as occurs during a stress test, the movement also interferes with the thoracic impedance, and the subsequent calculation of stroke volume and cardiac output. Previously thoracic impedance cardiography could only be performed on patients who were relatively motionless and apneic to avoid distorting the impedance data.

In addition, when this technique is applied to patients with severe cardiac dysfunction, the electrocardiogram signal and the thoracic impedance waveform may vary markedly from one cycle to another. A technique is required for determining whether a given set of data taken during the cardiac cycle is qualitatively sufficient from which to derive valid stroke volume and cardiac output results. Further, when such varying signals are to be averaged, a mechanism must be provided to normalize the signals so that deviations due to cardiac arrhythmia will not adversely affect the cardiac output computation.

SUMMARY OF THE INVENTION

An impedance cardiograph has a source of a high frequency excitation signal which is applied to two electrodes located on the upper body of a patient. Two additional electrodes are positioned intermediate the electrodes to which the excitation signal is applied and the latter electrodes are coupled to the input of an preamplifier. When a constant current is applied to the excitation electrodes, the voltage sensed between the second pair of electrodes is proportional to the thoracic impedance of the patient. The output from the preamplifier is rectified and filtered to produce a signal which corresponds to the instantaneous thoracic impedance. The rectified preamplifier output after additional processing, also is coupled to a differentiator to produce a signal corresponding to the first derivative (dZ/dt) of the thoracic impedance.

The impedance cardiograph also receives a conventional electrocardiograph signal, and optionally may receive a signal from a blood pressure monitor and from an piezoelectric microphone applied to the chest of the patient to produce a signal indicative of the heart sounds.

In the preferred embodiment, each of the signals representing the thoracic impedance, the derivative of the thoracic impedance (dZ/dt), ECG blood pressure and heart sounds are periodically sampled and the samples stored in a memory device for subsequent processing. The samples of the thoracic impedance derivative signal taken during each cardiac cycle are qualified against a predefined set of criteria to determine whether they are acceptable for further processing. Such qualification may include determining whether the interval between an R spike in the ECG signal and the minimum of the thoracic impedance derivative during the cardiac cycle has an acceptable value. Another qualification test is whether the interval that occurs between two defined points on the derivative signal during the cardiac cycle falls within an acceptable range of values. Specifically, the derivative waveform has a negative wave which commences after the QRS waveform in the ECG signal. The interval between the two midpoints on the falling and rising edges of this wave determine the interval for the second qualification test. Not only must this interval for a given cardiac cycle fall within a given range of values, but the interval must be within one standard deviation of the mean for a plurality of similar intervals for a number of cardiac cycles.

After the qualification process, the signal samples for the accepted derivative samples for the accepted cardiac cycles are ensemble averaged. In performing the ensemble averaging, the samples for each cardiac cycle are aligned about the signal sample having the minimum dZ/dt value. This ensemble averaged data is then employed using the Kubicek et al. equation along with the heart rate and average impedance derived from other signals produced by the monitor to calculate the stroke volume and cardiac output.

A general object of the present invention is to provide a impedance cardiograph which can be employed to measure at least one cardiac parameter, such as stroke volume and cardiac output.

A more specific object is to provide a cardiograph which eliminates the effects of respiration and body movement from the thoracic impedance data. This respiratory artifact removal is accomplished by ensemble averaging the impedance information.

Still another object of the present invention is to provide a mechanism for rejecting impedance data taken during cardiac cycles in which severe heart dysfunction occurred.

Yet another object is to learn patient ECG and impedance function waveforms for use in intelligent acquisition and analysis or data. This function allows the cardiograph to repeat measurements on the same patient with a minimum number of errors, maximum reproducibility, and minimum operator intervention.

DETAILED DESCRIPTION OF THE INVENTION

Figure 1:
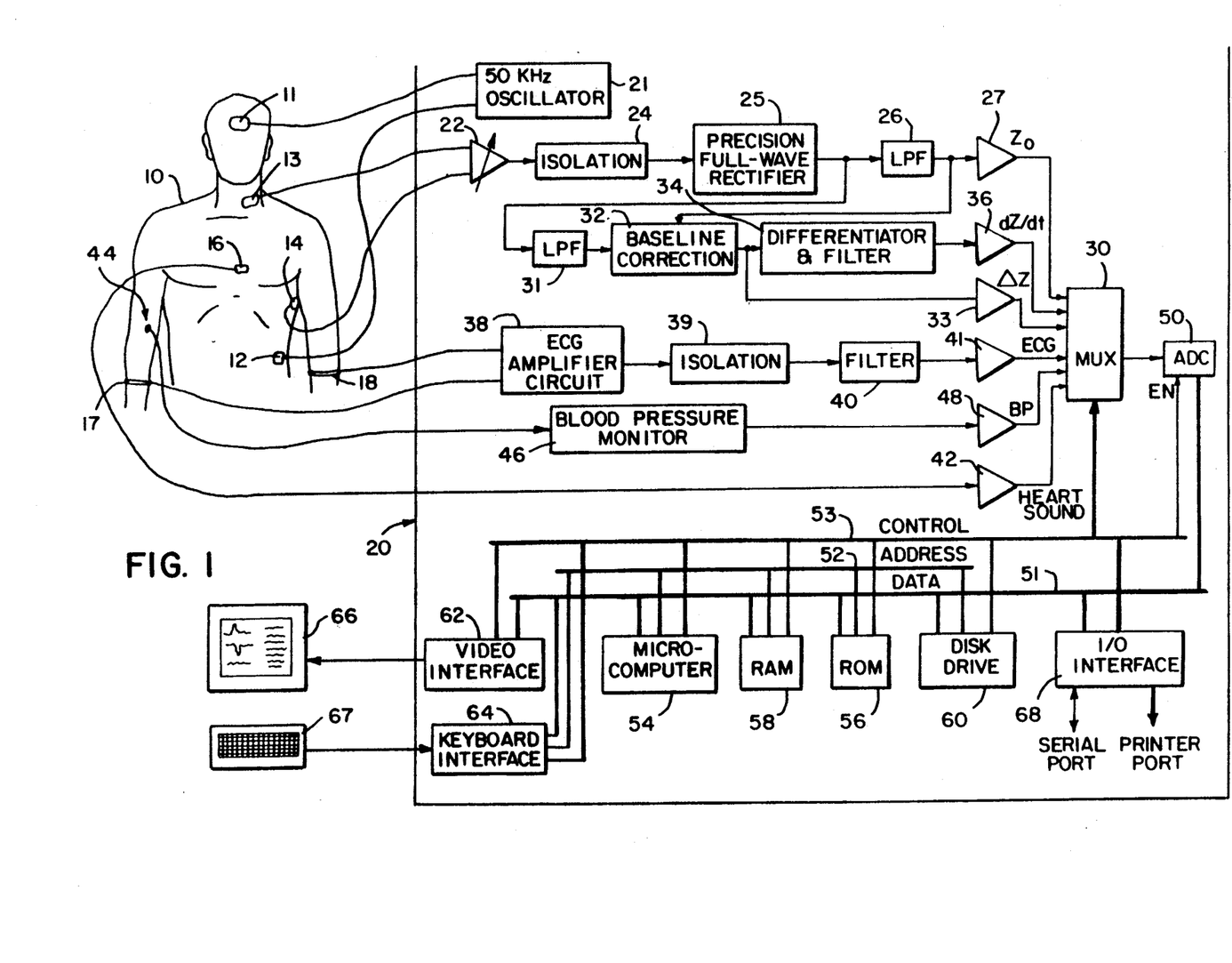
FIG. 1 is a block diagram of the circuitry for an impedance cardiograph according the present invention.

With initial to FIG. 1, the impedance cardiograph 20 is connected to a patient 10 by four patch electrodes 11-14. The first patch electrode 11 is applied to the patient's skin on the middle of the forehead. The second patch electrode 12 is positioned on the left mid-axillary line at the middle of the umbilicus. The first and second patch electrodes 11 and 12 are connected to the output of a 50 kHz oscillator 21. The third patch electrode 13 is positioned on the left side of the base of the patient's neck, and the fourth patch electrode 14 is located on the left mid-axillary line at the left of the xiphoid. The third and fourth patch electrodes 13 and 14 are connected to inputs of a sensing amplifier 22.

The signal from oscillator 21 coupled to the first and second patch electrodes 11 and 12 passes a constant current of approximately 500 microamperes RMS through the patient. This excitation establishes a series of equipotential surfaces through the patient perpendicular to the line extending between the two outer electrodes patch 11 and 12. By coupling the two inner electrodes patch 13 and 14 to sensing amplifier 22, the output of the amplifier corresponds to the voltage established between the inner electrodes by the excitation signal. Since the current introduced between the outer electrodes patch 11 and 12 is constant, the voltage sensed between the inner patch electrodes is proportional to the thoracic impedance of the patient. Furthermore, the electrical input impedance of amplifier 22 is very high (e.g. 10 megaohms) as compared to the impedance between the inner electrodes 13 and 14. Thus, negligible current will flow to the patch electrodes and negligible skin impedance will be measured. The gain of sensing amplifier 22 is variable to accommodate signal differences from pediatric and adult patients.

The output of amplifier 22 is passed through an isolation circuit 24 that electrically isolates the input electrodes from the monitor circuitry. The isolation not only safeguards the patient from voltage levels within the cardiograph 20, it protects the circuitry when the patient is being defibrillated or electrocauterized, as well as protecting from other voltage levels that might be accidentally applied. The amplifier output signal is rectified by a precision full-wave rectifier and then applied to a 0.7 Hz low-pass filter 26 to partially remove ventilation artifacts from the signal. The output from the first low-pass filter 26 is applied to a first output amplifier 27 to produce a signal corresponding to the absolute value of the baseline thoracic impedance ($Z_0$). The signal from first output amplifier 27 is applied to one input of a six-to-one multiplexer 30.

The output from the full-wave rectifier 25 also is coupled to a 50 Hz low-pass filter 31 which removes excitation artifacts from the rectified signal. The output of the filter 31 is connected to the input of a baseline correction circuit 32, along with the output signal from the first low-pass filter 26. The baseline correction circuit 32 performs auto-balancing to maintain the signal within an appropriate dynamic range. The output signal, designated $\Delta Z$, from baseline correction circuit 32 is applied via a second output amplifier 33 to a second input of the multiplexer 30. The baseline corrected signal also is differentiated and filtered in circuit 34 to produce the first derivative (dZ/dt) of the thoracic impedance. This differentiated signal is coupled through a third output amplifier 36 to another input of the multiplexer 30.

Two conventional ECG electrodes 17 and 18 are positioned on the patient's right and left arms, respectively, to sense signals produced by the heart. These ECG electrodes 17 and 18 are coupled to inputs of an electrocardiograph (ECG) amplifier circuit 38. Alternatively, for relatively healthy patients, the output of amplifier 22, filtered to remove the excitation signal component, can be coupled to the ECG amplifier circuit 38 in place of separate ECG electrodes 17 and 18. The output of the amplifier circuit 38 representing the ECG signal from the patient 10 is coupled by an isolation circuit 39 and filter 40 to the input of a fourth output amplifier 41. The output of the fourth output amplifier 41, representing the ECG signal, is connected to a third input of the multiplexer 30.

The heart sounds of the patient 10 are detected by a unidirectional piezoelectric microphone 16 applied against the patient's chest. The signal from the microphone 16 is coupled to a fifth output amplifier 42 to produce a signal indicative of the heart sounds, which is applied to another input of multiplexer 30.

Optionally, if the patient has an arterial catheter placed for direct measurement of blood pressure, as schematically indicated by point 44 on the patient's arm, the electrical signal from the catheter is coupled to a blood pressure monitor 46 to provide signals from which the systolic, diastolic and mean arterial blood pressures are derived. Alternatively, a signal from an external blood pressure monitor can be inputted into the cardiac monitor 20. As will be described, the blood pressure signal enables the derivation of the total peripheral blood flow resistance and the product of the flow rate and blood pressure as additional diagnostic parameters for the patient. The output of the blood pressure monitor 46 is applied to a sixth output amplifier 48 to produce a signal (BP) which is applied to the final input of the multiplexer 30.

Additional data acquisition channels can be provided for other physiological signals from the patient 10. For example, signals representing central venous pressure or from a finger phlethysmograph can be coupled to multiplexer 30 for processing.

As will be described, the multiplexer 30 sequentially selects each of the input signals and applies the selected signal to the input of an analog-to-digital converter (ADC) 50 which produces a multi-bit digital representation of the signal amplitude. The digital output of ADC 50 is coupled to a data bus 51. The monitor 20 also has an address bus 52 and a set of control lines forming a control bus 53.

The signal processing is performed by a microcomputer 54 which is connected to the three buses 51-53 to execute an analysis program stored in memories 56 and 58. Because of the amount of arithmetic processing being performed in the course of the data analysis, the microcomputer 54 includes a conventional math coprocessor to perform that computation as is well known in the computer fields. The raw data for analysis, which is supplied by the ADC 50, together with the results of the analysis and intermediate processing values are stored within a random access memory (RAM) 58. For longer term data storage, a hard disk drive 60 is provided. A floppy disk drive and back-up tape drive also can be included for archival storage of the acquired data and analysis results.

A video interface 62 is coupled to the data and the control buses 51 and 53 to provide a video signal for display on a monitor 66. A keyboard interface circuit 64 is provided so that the cardiograph operator can input control commands via a keyboard 67. The monitor 66 and keyboard 67 allow the operator not only to control the operation of the cardiograph 20, but also view the results of the analysis in several different display formats.

A remote I/O interface 68 is provided so that the data produced by the monitor may be printed or sent to another computer for storage. Similarly, the serial-port of the I/O interface 68 can permit a remote device to control the operation of the monitor 20 so that data may be acquired and analyzed on a periodic basis as determined by the remotely coupled device. The serial port also is used to transmit an alarm signal when the patient experiences a relatively sudden change in cardiac function, as will be described.

Once the electrodes and microphone have been properly applied to the patient and the leads connected to the cardiograph 20, the operator initiates the data acquisition phase via keyboard 67. The data may be acquired in any of several modes selectable by the operator. Initially, the operator must select the period during which the data will be acquired. For example, the period is defined in one second increments between five and thirty seconds, with ten seconds being a typical duration. Once the duration of the acquisition period has been set, the acquisition mode is chosen. The data acquisition may be initiated upon an operator's prompt, at set times of day, or after a fixed interval from the previous acquisition. Alternatively, the data may be acquired continuously with a new sampling period starting about five seconds after the previous one terminates. Other information required for data analysis, as will be described, also is entered at this time.

Figure 6A:
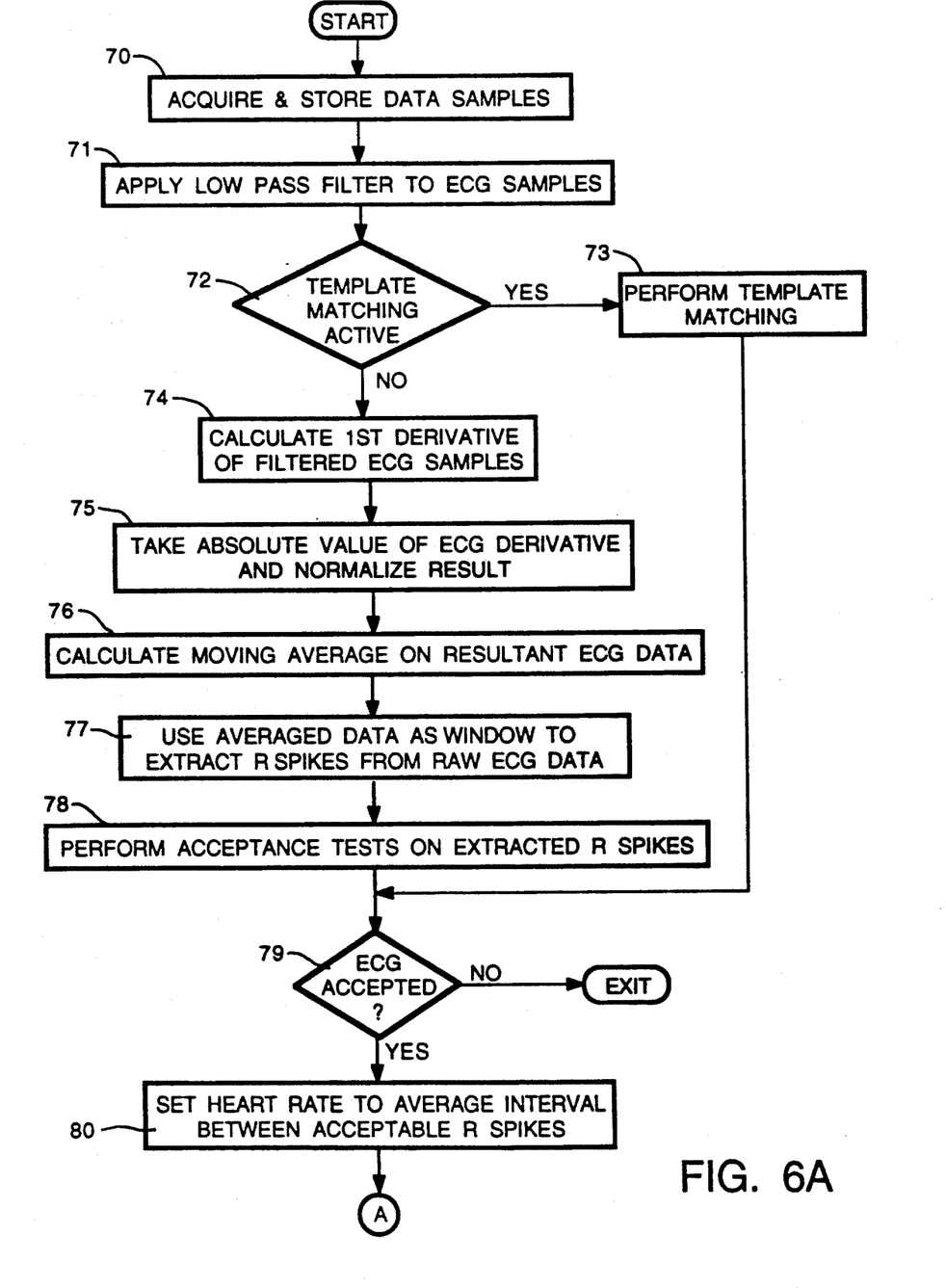
FIGS. 6A, B, and C depict a flowchart of the software for analyzing the signals acquired from the patient.

With reference to FIGS. 1 and 6A, after the operational parameters have been entered, the operator enters a command via keyboard 67 to initiate the data acquisition and storage as depicted by step 70 on the flowchart of FIG. 6A. During this time, the thoracic impedance, ECG, blood pressure and heart sound signals are coupled to the respective inputs of multiplexer 30. The microcomputer 54 sends control signals via bus 53 to the multiplexer 30 causing the sequential connection of a different multiplexer input signal to the ADC 50. Once a given connection is complete and the ADC 50 has had sufficient time to digitize the signal, the microcomputer 54 issues an enable signal to the ADC causing its output to be applied to the data bus 51. This digitized sample of the selected signal then is stored within a section of RAM 58 which is designated for storage of such signal samples. Specifically, sections of the RAM 58 have been designated for sample storage of the thoracic impedance $Z_0$, the differentiated impedance dZ/dt, ECG, blood pressure and heart sound signals. At the end of the data acquisition period, the microcomputer 54 terminates the control signals to the multiplexer 30 and the ADC 50 and can commence analysis of the data.

The first phase of analyzing the stored data involves qualifying the data taken during each cardiac cycle, based on the validity of the ECG samples and the differentiated impedance samples. The first step 71 in this process involves digitally applying a low-pass filter to the ECG signal samples stored within RAM 58 to remove from the signal any artifacts due to high frequency noise affecting the signal from the patient.

The program execution advances to step 72 where a determination is made whether a QRS wave template matching function is active. For the initial sets of data samples from a patient, this feature will be inactive and the program execution advances directly to step 74. After ECG samples have been acquired over several cardiac cycles, the operator can activate the template matching via an entry into the keyboard 67. At that time the operator accepts one of the initial electrocardiogram QRS waveforms as normal for that patient. The data for this waveform is stored in RAM 58 as a normal reference QRS waveform "template" against which subsequently acquired QRS waveforms will be compared to test for shape similarity at step 73. This is accomplished using conventional least squares regression analysis to determine a chi-squared value to measure the goodness, or degree, of fit. The program then advances to step 79 where QRS waveforms with chi-square values in excess of 1.5 are rejected as artifacts which are not representative of that patient's cardiac function.

When template matching is inactive, the program branches from step 72 to step 74. A first derivative of the filtered ECG signal is calculated and at step 75 the absolute value of the derivative is normalized so that the samples will represent a one volt peak to peak signal. A moving average then is taken of the ECG samples by using either a five point moving average or a fifty millisecond moving average interval at step 76.

Figure 2:
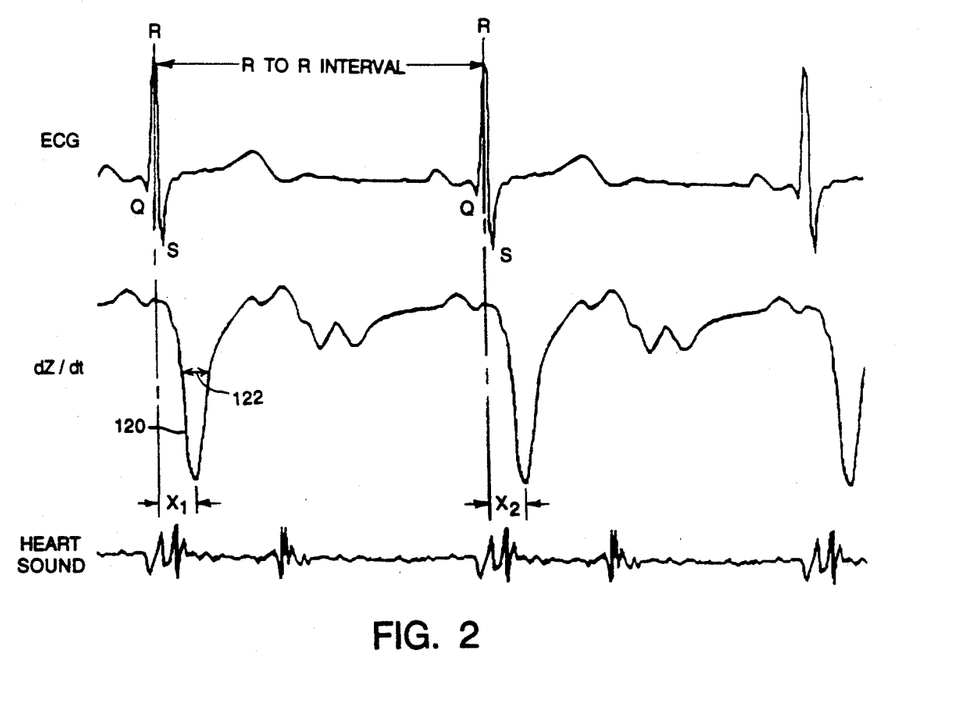
FIG. 2 represents the electrocardiogram, thoracic impedance and heart sound waveforms sensed by the cardiograph during two consecutive cardiac cycles.

The signal processing of steps 74–76 produces a resultant set of ECG data samples which have non-zero values in storage locations which correspond to the "R" spikes of the QRS waveforms in the ECG samples (see FIG. 2). At step 77, this resultant set of data samples is used as a mask to identify the RAM locations containing signal samples for the R spikes in the acquired ECG data. Because each sample of the ECG signal was stored at fixed intervals, the RAM storage locations provide temporal information regarding the ECG signal. As a result, the number of locations between those at which the R spike samples of greatest magnitude are stored provides a measurement of the time interval between the occurrence of the R spikes in the QRS cardiogram waveform and therefore the heart rate. Similarly, because each of the other signals acquired from the patient were time division multiplexed with the ECG signal, there is a temporal correlation between signal samples stored for those signals in the other storage sections of RAM 58. For example, knowing at which storage location the peak of an R spike of the ECG signal is stored allows locating the sample of the dZ/dt signal which occurred at substantially the same instant of time as that R spike peak. This temporal relationship between the storage locations and the signal samples contained therein is used in the computation of cardiac stroke and output, as will be described.

The ECG data for each cardiac cycle must meet a defined set of criteria at step 78, in order for data from that cycle to be used in subsequent analysis. Specifically, once the locations of the R spikes have been determined, the interval between each R spike is determined to verify that it is at least two milliseconds in duration and that each interval is within one standard deviation of the average R to R interval. Furthermore, the width of each R spike must be greater than two milliseconds and less than 18 milliseconds and the height of the R wave must exceed 68 percent of the full scale signal magnitude This R wave height threshold is user adjustable for research applications.

Each ECG cycle which meets the qualification criteria is marked as valid for use in subsequent signal processing. For example, a flag or other indication may be stored for each cardiac cycle within RAM 58 indicating whether the data taken during the cycle is valid or invalid. If an insufficient number of R spikes meets the qualification criteria as determined at step 79, the program will exit and notify the operator that too few ECG cycles were detected. Otherwise, the analysis program advances to step 80 where the microcomputer 54 calculates the heart rate as the average interval between R spikes of valid consecutive cardiac cycles.

The program execution then advances to a section which qualifies the differentiated thoracic impedance data for further analysis. In explaining the qualification of this impedance data, reference will be made to FIG. 2, which in the top waveform illustrates the ECG signal samples, the middle waveform represents the differentiated impedance signal data (dZ/dt), and the lower waveform represents the heart sound signal samples.

Figure 6B:
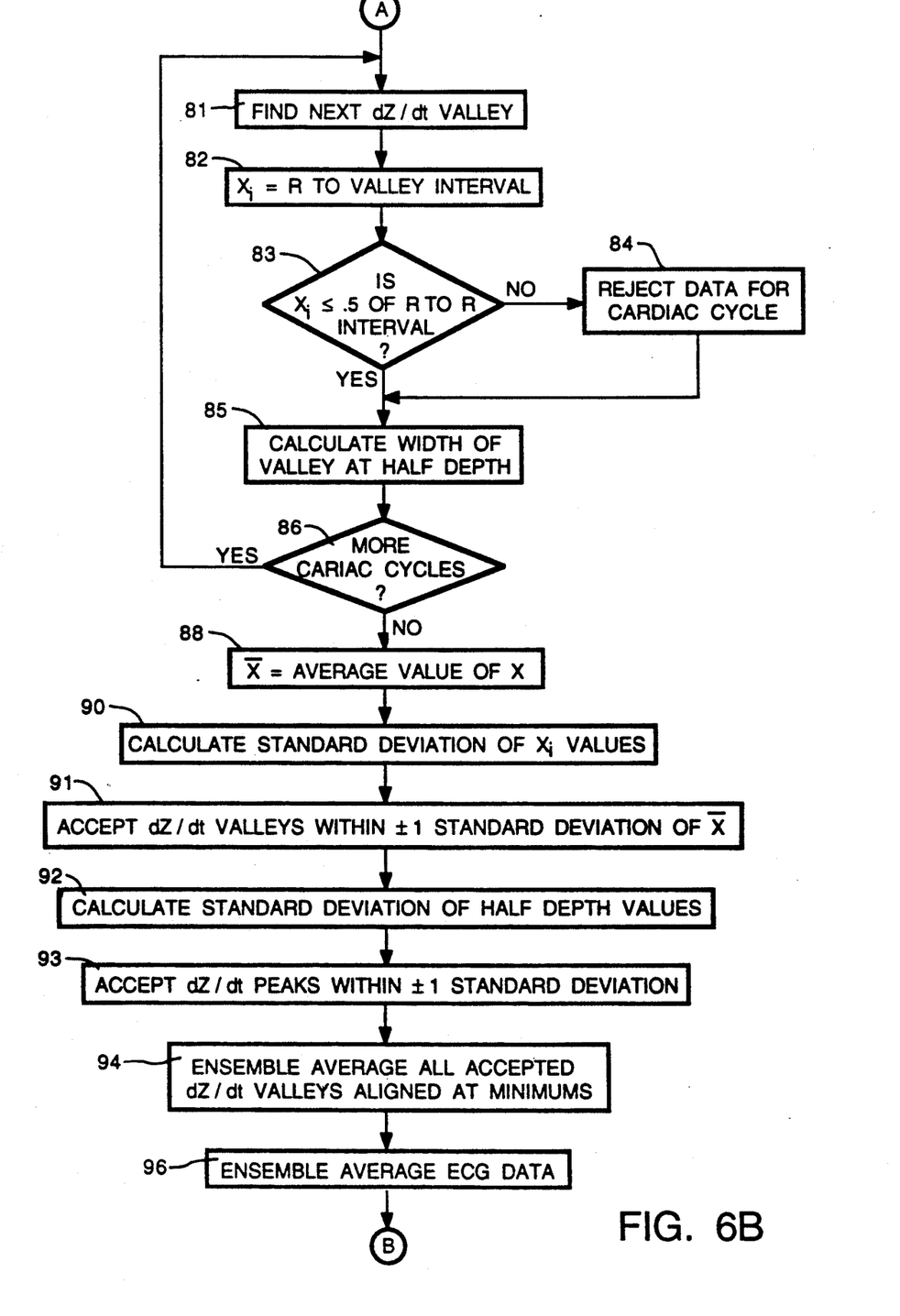

Referring to step 81 on FIG. 6B, the microcomputer 54 begins examining each of the data samples for the differentiated impedance signal dZ/dt to find the first valley 120 (or negative going wave) in the signal samples. Cardiologists commonly refer to this decrease in thoracic impedance as a peak since it corresponds inversely to the ejection rate which has a maximum value when the minimum dZ/dt value occurs. Once the minimum dZ/dt value has been found in the first cycle, the time interval $X_1$ between the occurrence of the corresponding R spike in the ECG waveform and the minimum dZ/dt point is calculated at step 82. The interval $X_1$ then is compared to the corresponding R to R interval for that cardiac cycle at step 83. If the value of $X_1$ is more than fifty percent of the R to R interval, the data for that cardiac cycle is rejected at step 84. When the value of $X_1$ does not meet this criterion, the cardiac cycle data validity flag stored in RAM 58 is reset to indicate the rejection of the dZ/dt data acquired during this cardiac cycle.

Next, the width of the dZ/dt waveform valley at half its depth, as indicated by line 122 in FIG. 2, is determined at step 85. For example, this determination may be made by first deriving the arithmetic mean between the highest and lowest points of the waveform's valley 120. Then, the dZ/dt data samples on either side of the valley minimum with values closest to that mean value are found. These two samples correspond to the mid-depth points on the falling and rising edges of the valley. The number of samples existing between the ones found at the mid-depth points correspond to the half-dept width. After the dZ/dt data for the first cardiac cycle have been examined the microcomputer at step 86 checks whether data for additional cardiac cycles remain to be examined. If so, the program execution returns to step 81 to calculate the interval $X_i$ and the valley half-depth width for the next cardiac cycle.

After each cardiac cycle of dZ/dt data has been processed in this manner, a further validation of the dZ/dt data is performed at steps 88 through 93. Initially the arithmetic mean value ($\overline{X}$) of the $X_i$ intervals is determined at step 88 and the standard deviation of the $X_i$ intervals is derived at step 90. At step 91 each $X_i$ interval is checked and only the dZ/dt data for cardiac cycles with intervals within plus or minus one standard deviation of the mean value $\overline{X}$ are accepted at step 91. Then at step 92, the standard deviation for the half-depth widths is calculated. The dZ/dt data for each cardiac cycle are accepted at step 93 only if the valley half-depth width is within plus or minus two standard deviations of the mean half-depth width.

Figure 3:
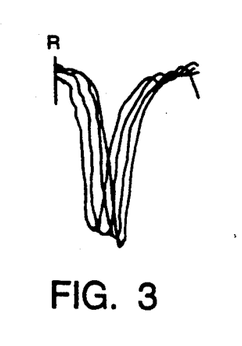
FIG. 3 graphically illustrates the application of conventional ensemble averaging to the thoracic impedance signals for several cardiac cycles.

At step 94, the dZ/dt data for each accepted cardiac cycle is ensemble averaged. The straight forward ensemble averaging technique would align the group of signal samples for each of the accepted cardiac cycles by aligning the signal samples of the dZ/dt waveform which occur at the same time as the R spike in the ECG signal for that cardiac cycle. However, a problem occurs when this ensemble averaging technique is used with data from patients with severe heart dysfunction. In such patients, the interval $X_i$ between the occurrences of the R spike and the dZ/dt waveform minimum varies significantly among the cardiac cycles. Thus, the data for each dZ/dt valley may be offset temporally in the averaging process, as shown in FIG. 3, thereby producing an inaccurate ensemble average of the waveform data.

Figure 4:
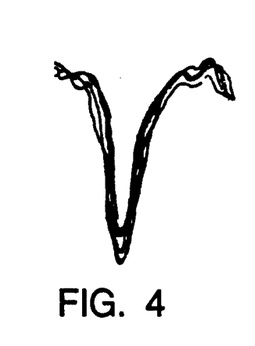
FIG. 4 graphically illustrates peak coincident ensemble averaging of the thoracic impedance signal for several cardiac cycles.

Rather than using the straight forward ensemble averaging technique, the present system aligns the dZ/dt data for each cardiac cycle at the minimum point of each valley, as illustrated in FIG. 4. In order to arithmetically perform the ensemble averaging, the microcomputer 54 finds location within RAM 58 at which the minimum dZ/dt data sample for each cardiac cycle was stored. The microcomputer then accesses a data sample taken a fixed number of samples before the minimum dZ/dt sample and reads a given number of consecutive samples from RAM 58 from this latter sample. The same ordinally read dZ/dt data samples from the different cardiac cycles are averaged together to produce ensemble averaged signal data, as graphically depicted by the middle waveform (dZ/dt) in FIG. 5. This technique is referred to herein as "peak aligned ensemble averaging", as the data is aligned about the peaks of the negative going wave in the dZ/dt data.

Figure 6C:
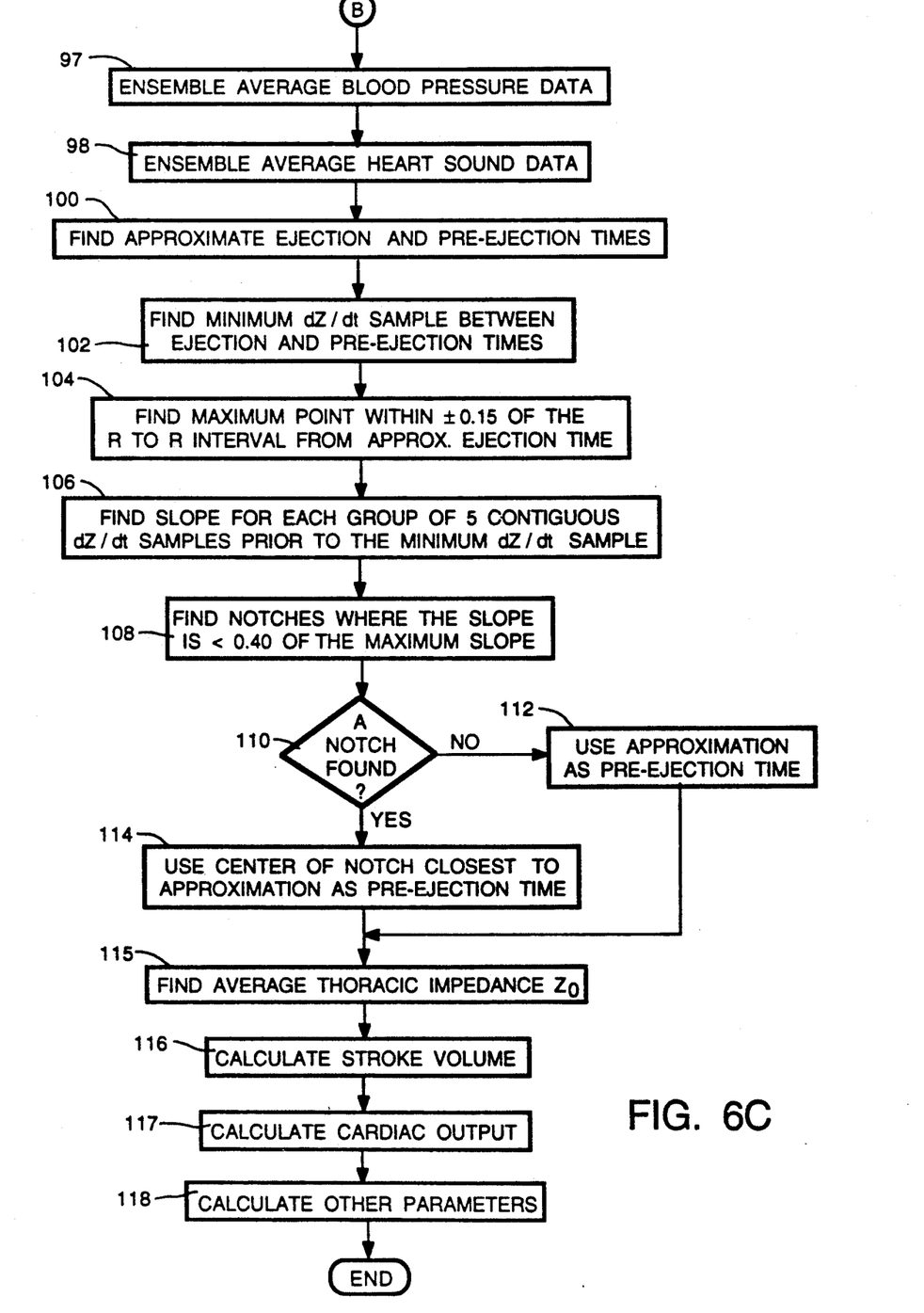

Thereafter, the ECG signal samples for each cardiac cycle are ensemble averaged at step 96 by commencing the averaging with the R spike at the beginning of each cardiac cycle. Similarly, at steps 97 and 98 of FIG. 6C, the blood pressure data and heart sound data are ensemble averaged by aligning the samples for each cardiac cycle which occur at the same time as the R spike in the ECG signal for that cycle. The different sets of ensemble averaged data are stored in the disk drive 60.

Figure 5:
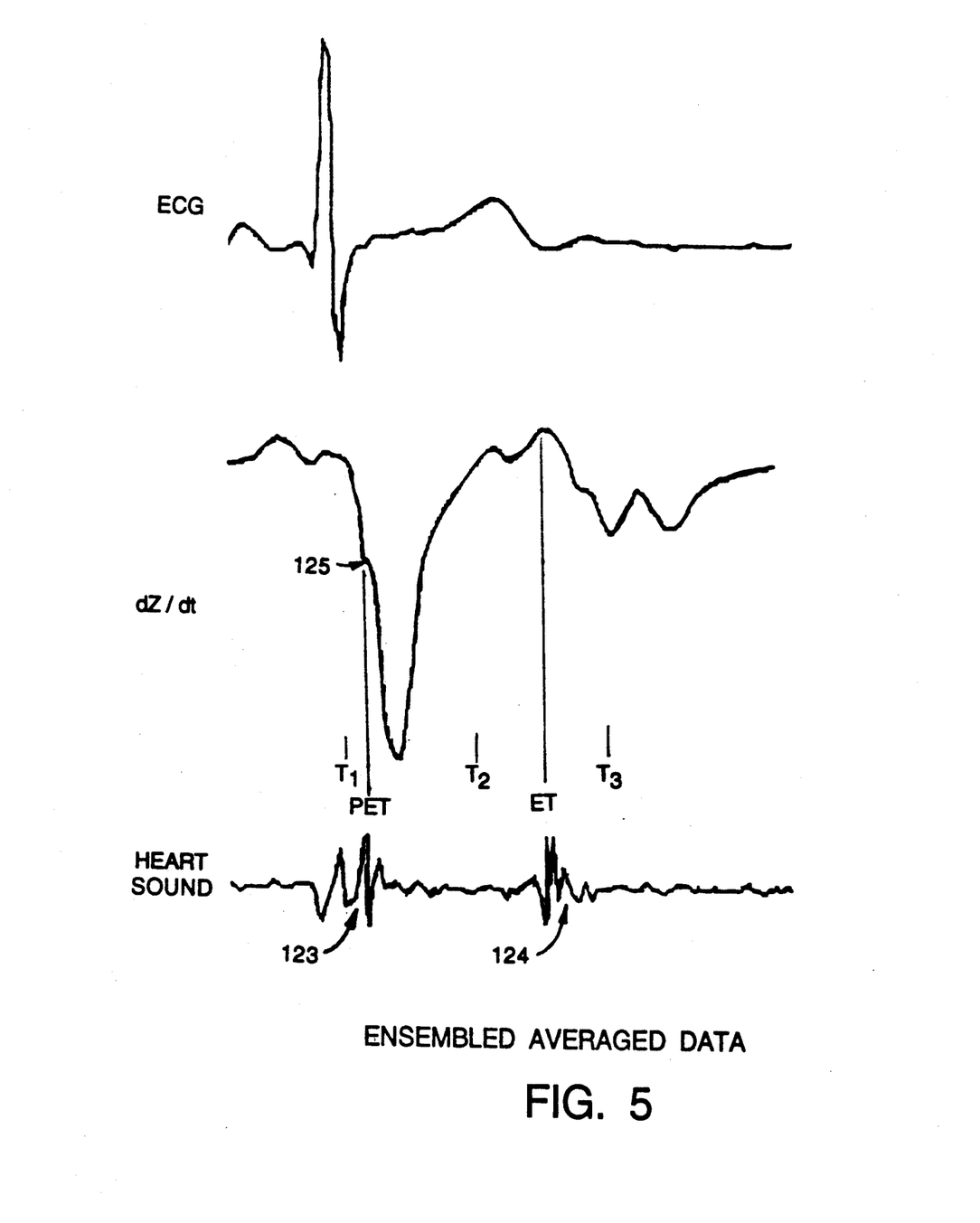
FIG. 5 represents the resultant ensemble averaged ECG, thoracic impedance and heart sound signals.

FIG. 5 graphically depicts the ensemble averaged ECG, dZ/dt, and heart sound waveforms. From this collection of ensemble averaged data, the cardiac pre-ejection time (PET) and the ejection time (ET) are found. To do so, the approximate times for the ejection and pre-ejection are determined from the heart rate using Whieissler's function, A. M. Whieissler et al., "Systolic Time Intervals in Heart Failure in Man"; Circulation, Vol. 37, 1968, pp. 149-159. Using the samples of the averaged dZ/dt data which occur at these times as end points, the data sample in between are inspected to find the sample having the minimum value at step 102. This minimum valued sample corresponds to the lowest value in the valley of the peak aligned ensemble averaged dZ/dt waveform.

Then at step 104, the data samples located about the approximated ejection time (ET) are inspected to find the true maximum point near that approximated time. Specifically, times $T_2$ and $T_3$ are defined as occurring at plus and minus 15 percent of the average R to R interval from the approximated ejection time. Alternatively, the duration of the "dub" wave 124 in the ensemble averaged heart sound data can be used as defining interval $T_2$-$T_3$. The data samples taken during the interval $T_2$-$T_3$ are analyzed by the microcomputer 54 to determine the sample with the largest magnitude within that interval. This maximum sample indicates the actual ejection time during the cardiac cycle. A representation of the relative time during the cardiac cycle at which this maximum saddle occurred is stored in RAM 58 for subsequent use.

A different approach is employed to find the actual pre-ejection time. At step 106, the approximated pre-ejection time is used to define a time T1 which occurs four percent of the R to R interval prior to the approximated pre-ejection time. Alternatively, the first positive peak in the "lub" wave 123 of the ensemble averaged heart sound data can be employed to define time $T_1$. The slope for each group of five consecutive dZ/dt samples in the interval from T1 to when the minimum dZ/dt sample occurs is calculated and stored temporarily in RAM 58. The microcomputer 54 then inspects this slope data to find notches (e.g. notch 125) in the waveform where the slope is less than forty percent of the steepest slope within this interval.

At step 110, if a notch was not found within the waveform, the program execution branches to step 112 where the approximation derived at step 100 is used as the actual pre-ejection time. However, if a notch was found, the program advances to step 114. If only one notch was found, then the center data sample of the five which form the notch is used as defining the pre-ejection time. However, if multiple notches exist, the center data point for the notch closest to the approximated pre-ejection time is used as defining the actual ejection time. The final ejection and pre-ejection times are used to derive the cardiac ejection interval which occurs between these times. The operator may override the program's pre-ejection selection by manually selecting the correct pre-ejection point via keyboard 67.

Next at step 115, the raw thoracic impedance data $Z_0$ is averaged. The program execution advances to step 116 where the stroke volume is calculated using the Kubicek equation given above. In doing so, the resistivity of the blood is set at a default value of 150 ohms/cm, unless a different value is set by the operator. Similarly, the distance between the sensing electrodes 13 and 14 is either a predefined fixed distance or the actual distance is fed into the keyboard 67 during initial setup of cardiograph 20. The stroke volume is multiplied by the heart rate determined previously to produce a value for the cardiac output at step 117. The microcomputer 54 then calculates other parameters, such as systolic time intervals using the blood pressure information, total peripheral resistance, and the cardiac index. The results of these calculations are stored in the disk drive 60 before the analysis program ends.

In some patients with severe heart dysfunction, the ECG signal may be so poor that the R spike of the QRS wave cannot be used in the process described above. In this case, the samples of the blood pressure data which indicate the systolic pressure are used in place of the ECG signal sample for the peak of the R spike. The method remains the same with intervals $X_i$ being calculated from the maximum blood pressure data samples.

Once the analysis is complete, the results of the data are formatted and displayed on monitor 66 or sent via the I/O interface 68 to a printer.

The present cardiograph 20 can be utilized to provide round-the-clock monitoring of patients within an intensive care unit. Typically in this case, the cardiograph is configured to periodically acquire samples from the patient for analysis. For example, the samples may be acquired once every 15 or 30 minutes. Following each analysis, one or more calculated values for stroke volume, cardiac output and other parameters are compared with previous values to generate trend data. Specifically, the samples are compared to determine there is a continuing increase or decrease in the magnitude of a given parameter, such as, cardiac output. In such a case, should a new value for cardiac output differ significantly from previous values, a warning indication is presented via monitor 66 or through the I/O interface 68 to alert medical personnel of a significant change in the condition of the patient. In addition, the slope of the cardiac output values can be computed. Should this slope exceed a predetermined threshold value, for example a 5 percent positive or negative slope, a similar alarm may be sent to medical personnel.

Trend values are calculated for cardiac output, heart rate, thoracic impedance ($Z_0$), and total peripheral resistance. A graph of all trend data is alternately presented on the monitor 66 at the operator's command. During continuous monitoring, five sets of ensemble averaged data are combined to derive mean values for use in calculating and displaying trends.

Changes in the baseline thoracic impedance, $Z_0$, indicate change in the total amount of thoracic fluid volume in the patient and can be a significant and prompt indication of clinical complications. The trend calculations and graphic displays for baseline thoracic impedance are therefore also monitored, stored to disk and alarmed if the patient's original $Z_0$ value has changed more than ten percent. The same principle of calculating mean values from five consecutive samples of $Z_0$ is utilized to eliminate quick changes due to patient artifacts.

In lieu of the dZ/dt minimum peak height measurement of the dZ/dt waveform magnitude, a more sensitive and reproduceable technique has been developed using the actual area under the ensemble averaged dZ/dt waveform. This dZ/dt curve area algorithm is more accurate for patients with abnormal dZ/dt waveforms, especially when there is a notch or irregular shape at the approximate location of $dZ/dt_{max}$. This value is substituted for the expression ($dZ/dt_{max}$ times ejection time) in the Kubicek stroke volume equation.

To determine the volume of blood which regurgitates back into the ventricle after the ejection time, the area under the dZ/dt curve which is above the dZ/dt baseline value between the end of ejection market and the next negative crossing of the dZ/dt waveform is calculated and ratioed to the dZ/dt cardiac stroke volume for an absolute reference value.

We claim:

1. An impedance cardiograph comprising:
  means for applying an excitation signal to the thorax of an animal;
  means, responsive to the excitation signal, for producing a first electrical signal which varies with thoracic impedance changes of the animal;
  means for producing a second electrical signal that corresponds to the first derivative of the first electrical signal;
  means for generating a plurality of periodic samples of the second electrical signal, the samples being divided into a number of groups with the samples in each group representing the second electrical signal during a different cardiac cycle of the animal;
  means for identifying a signal sample in each group which occurs during a cardiac ejection interval and which corresponds to the smallest rate of change of the thoracic impedance;
  means for ensemble averaging the groups of the samples of the second electrical signal to produce a set of ensemble averaged signal samples, said means for ensemble averaging aligning each group of samples of the second electrical signal about a sample in each group which occurs during a cardiac ejection interval and which corresponds to the smallest rate of change of the thoracic impedance; and
  means for computing a cardiac performance parameter value from the ensemble averaged signal samples.

2. The impedance cardiograph as recited in claim 1 further comprising means for selecting the groups of samples of the second electrical signal for ensemble averaging based upon whether each group of samples meets a predefined acceptance criteria.

3. The impedance cardiograph as recited in claim 2 wherein said means for selecting includes:
  means for measuring an interval between samples of a group which correspond to two predefined points on the second electrical signal; and
  means for determining whether the interval for each group is within a predefined range of values.

4. The impedance cardiograph as recited in claim 2 further comprising a means for producing an electrocardiogram signal having a QRS wave during each cardiac cycle.

5. The impedance cardiograph as recited in claim 4 wherein said means for selecting includes:
  means for measuring an interval between a reference point on the QRS wave and a predefined point on the second electrical signal during each of the cardiac cycles; and
  means for determining whether the measured interval is within a predefined range of values.

6. The impedance cardiograph as recited in claim 4 wherein said means for selecting includes:
  means for measuring a first interval point on the QRS wave and a predefined point on the second electrical signal during each of the cardiac cycles; and
  means for determining whether the measured interval is within one standard deviation of an arithmetic mean of a plurality of first intervals.

7. The impedance cardiograph as recited in claim 6 wherein said means for selecting further includes:
  means for measuring a second interval between a reference point on two consecutive QRS waves in the electrocardiogram signal; and
  means for determining whether the first interval is less than a given fraction of the second interval.

8. The impedance cardiograph as recited in claim 4 wherein said means for selecting includes:
  means for determining whether a QRS wave has a duration that is within an given range of values; and
  means for determining whether a QRS wave has a height that is within an given range of values.

9. The impedance cardiograph as recited in claim 4 wherein said means for selecting includes:
  means for selecting a QRS wave as a reference QRS wave;
  means for deriving a shape fit value representing the degree to which another QRS wave matches the reference QRS wave; and
  means for determining whether the shape fit value is within a given range of shape fit values.

10. The impedance cardiograph as recited in claim 4 wherein said means for selecting includes:
  means for measuring intervals between a reference point on each consecutive QRS wave in the electrocardiogram signal; and
  means for determining whether each interval is within a given range of standard deviations of an arithmetic mean of a plurality of the intervals.

11. The impedance cardiograph as recited in claim 2 further comprising a means for sensing blood pressure of the animal.

12. The impedance cardiograph as recited in claim 11 wherein said means for selecting includes:
  means for measuring a first interval between the occurrence of systolic blood pressure and a predefined point on the second electrical signal during each of the cardiac cycles; and
  means for determining whether each measured interval is within a defined range of reference values.

13. The impedance cardiograph as recited in claim 12 wherein the defined range of reference values is specified by a given number of standard deviations of an arithmetic mean of a plurality of the first intervals.

14. The impedance cardiograph as recited in claim 12 wherein said means for selecting further includes:
  means for measuring a second interval between consecutive occurrences of systolic blood pressure; and
  means for determining whether the first interval is less than a given fraction of the second interval.

15. An impedance cardiograph comprising:

means for applying an excitation signal to the thorax of an animal;

means, responsive to the excitation signal, for producing an electrical signal which varies with thoracic impedance changes of the animal;

means for producing an electrocardiogram signal containing a cardiac QRS wave;

means for determining a heart rate of the animal from the electrocardiogram signal;

means for selecting segments of the electrical signal for which a predefined point of a segment occurs within a given interval from an occurrence of a predetermined point on a cardiac QRS wave, said means for selecting including means for determining the given interval; and means, responsive to said first means for selecting, for computing a cardiac performance parameter value from the selected segments of the electrical signal.

16. The impedance cardiograph as recited in claim 15 wherein the predetermined point on a cardiac QRS wave is a peak of an R spike.

17. The impedance cardiograph as recited in claim 16 wherein the predefined point of a segment of the electrical signal corresponds to the smallest rate of change of the thoracic impedance.

18. An impedance cardiograph comprising:
means for applying an excitation signal to the thorax of an animal;
means, responsive to the excitation signal, for producing a first electrical signal which varies with thoracic impedance changes of the animal;
means for producing a second signal corresponding to the first derivative of the first electrical signal;
means for producing an electrocardiogram signal having a QRS wave during each cardiac cycle;
means for generating a plurality of periodic samples of the first electrical signal, second electrical signal and the electrocardiogram signal, the samples of each signal being divided into a number of groups with the samples in each group representing the respective signal during a different cardiac cycle of the animal;
means for averaging the samples of the first electrical signal to produce an average thoracic impedance value;
means for ensemble averaging the groups of the samples of the second electrical signal to produce a first set of ensemble averaged signal samples, said means for ensemble averaging aligning each group of samples of the second electrical signal about a sample in each group which occurs during a cardiac ejection interval and which corresponds to the smallest rate of change of the thoracic impedance;
means for ensemble averaging the groups of the samples of the electrocardiogram signal to produce a second set of ensemble averaged signal samples; and
means for computing cardiac stroke volume from the first set of ensemble averaged signal samples and the average thoracic impedance value.

19. The impedance cardiograph as recited in claim 18 further comprising means for displaying the first and second sets of ensemble averaged signal samples.

20. The impedance cardiograph as recited in claim 18 further comprising means for selecting the groups of samples of the second electrical signal for ensemble averaging based upon whether each group of samples meets a predefined acceptance criteria.

21. The impedance cardiograph as recited in claim 20 wherein said means for selecting includes means for determining whether each cardiac cycle has a duration within a first predefined range of values; and whether the QRS wave has a duration within a second predefined range of values.

22. The impedance cardiograph as recited in claim 20 wherein said means for selecting includes:
means for selecting a QRS wave as a reference QRS wave;
means for deriving a shape fit value representing the degree to which another QRS wave matches the reference QRS wave; and
means for determining whether the shape fit value is within a given range of shape fit values.

23. The impedance cardiograph as recited in claim 20 wherein said means for selecting includes:
means for measuring an interval between a reference point on the QRS wave and a predefined point on the second electrical signal during each of the cardiac cycles; and
means for determining whether the measured interval is within a predefined range of values.

24. The impedance cardiograph as recited in claim 20 wherein said means for selecting includes:
means for measuring an interval between samples of a group which correspond to two predefined points on the second electrical signal; and
means for determining whether the interval for each group is within a predefined range of values.

25. A method of measuring cardiac activity in an animal comprising:
applying an excitation signal to the thorax of the animal;
producing a first electrical signal which varies with thoracic impedance changes of the animal;
producing a second electrical signal corresponding to a first derivative of the first electrical signal;
generating a plurality of periodic samples of the second electrical signal, the samples being divided into a number of groups with the samples in each group representing the second electrical signal during a different cardiac cycle of the animal;
identifying in each group a signal sample which occurs during a cardiac ejection interval and which corresponds to the smallest rate of change of the thoracic impedance;
aligning each group of samples of the second electrical signal about a sample in each group which occurs during a cardiac ejection interval and which corresponds to the smallest rate of change of the thoracic impedance, and ensemble averaging the aligned groups of the samples of the second electrical signal to produce a set of ensemble averaged signal samples; and
computing a cardiac performance parameter value from the ensemble averaged signal samples.

26. The method of measuring cardiac activity as recited in claim 25 further comprising selecting the groups of samples of the second electrical signal for ensemble averaging based upon whether each group of samples meets a predefined acceptance criteria.

27. The method of measuring cardiac activity as recited in claim 26 wherein selecting step includes:
measuring an interval between samples of a group which correspond to two predefined points on the second electrical signal; and determining whether the interval for the group is within a predefined range of values.

28. The method of measuring cardiac activity as recited in claim 26 further comprising producing an electrocardiogram signal, which signal has a QRS wave during each cardiac cycle.

29. The method of measuring cardiac activity as recited in claim 28 wherein said selecting step includes:
determining whether each cardiac cycle has a duration within a first predefined range of values; and
determining whether each QRS wave has a duration within a second predefined range of values.

30. The method of measuring cardiac activity as recited in claim 28 wherein said selecting step includes:
measuring an interval between a reference point on the QRS wave and a predefined point on the second electrical signal during each cardiac cycle; and
determining whether each measured interval is within a defined range of values.

31. The method of measuring cardiac activity as recited in claim 26 wherein said selecting step includes:
producing an electrocardiogram signal having a QRS wave during each cardiac cycle;
selecting a QRS wave as a reference QRS wave;
deriving a shape fit value representing the degree to which another QRS wave matches the reference QRS wave; and
determining whether the shape fit value is within a given range of shape fit values.

32. The method of measuring cardiac activity as recited in claim 25 wherein said step of computing a cardiac performance parameter value includes calculating the stroke volume.

33. The method of measuring cardiac activity as recited in claim 25 wherein said step of computing a cardiac performance parameter value includes calculating cardiac output.

34. The method of measuring cardiac activity as recited in claim 25 further comprising evaluating a plurality of cardiac performance parameter values, and determining whether the evaluation indicates an undesirable trend in the cardiac activity of the animal.

35. An impedance cardiograph comprising:
means for applying an excitation signal to the thorax of an animal;
means, responsive to the excitation signal, for producing an electrical signal which varies with thoracic impedance changes of the animal;
means for producing an electrocardiogram signal containing a cardiac QRS wave;
means for determining a heart rate of the animal from the electrocardiogram signal;
means for measuring an interval between two predefined points within a segment of the electrical signal;
means for selecting segments of the electrical signal, a given segment being selected in response to a measurement of the interval of the segment being within a given range of values; and
means, responsive to said first means for selecting, for computing a cardiac performance parameter value from the selected segments of the electrical signal.

36. The impedance cardiograph recited in claim 35 wherein said means for selecting acquires measurements of intervals for segments from a plurality of cardiac cycles, and the given range of values is defined by a number of standard deviations from an arithmetic mean of the acquired measurements.

37. The impedance cardiograph as recited in claim 35 wherein the two predefined points correspond to half-height points on a peak in the electrical signal segment.

* * * * *